(12) United States Patent
Sasaki et al.

(10) Patent No.: US 7,833,487 B2
(45) Date of Patent: Nov. 16, 2010

(54) SOLUTION FILLING APPARATUS

(75) Inventors: Jun Sasaki, Kawasaki (JP); Kazuo Tamamushi, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 1052 days.

(21) Appl. No.: 11/399,626

(22) Filed: Apr. 7, 2006

(65) Prior Publication Data

US 2007/0175758 A1    Aug. 2, 2007

(30) Foreign Application Priority Data

Jan. 31, 2006    (JP) .............................. 2006-023710

(51) Int. Cl.
*B01L 3/02*    (2006.01)

(52) U.S. Cl. .......................... 422/100; 422/63; 422/65; 422/99; 436/180; 436/43; 700/1; 700/108; 700/95; 700/245

(58) Field of Classification Search ..................... 700/1, 700/108, 95, 245; 702/182; 422/63–67, 422/99–100; 436/43, 180
See application file for complete search history.

(56) References Cited

U.S. PATENT DOCUMENTS

| | | | | |
|---|---|---|---|---|
| 5,032,381 | A | * | 7/1991 | Bronstein et al. .............. 435/4 |
| 5,294,325 | A | * | 3/1994 | Liu .............................. 204/418 |
| 5,403,554 | A | * | 4/1995 | Freeman ..................... 422/100 |
| 5,487,825 | A | | 1/1996 | Kurze et al. |
| 6,621,191 | B1 | | 9/2003 | Nomura et al. |
| 2004/0235143 | A1 | | 11/2004 | Sasaki et al. |

FOREIGN PATENT DOCUMENTS

| | | |
|---|---|---|
| JP | 5-261852 | 10/1993 |
| JP | 07-061074 | 3/1995 |
| JP | 2001-26000 | 1/2001 |
| JP | 2004-344036 | 12/2004 |

OTHER PUBLICATIONS

Tokai Kogyosho Co., Ltd., "Nano-Automatic Injection Apparatus," [Online], Web URL: <http://www.chubu.meti.go.jp/technology/catalogue/bio_medical_007.pdf>.
Ichiro Jimon et al., "Establishment of Technique for producing a Transgenic Mouse at the Institution," Shiga University of Medical Science, [Online], Web, URL: <http://www.shiga-med.ac.jp/~gijutsu/4nittei/01houkoku/01tera.html>.
Masuda, (First Draft: Tabuchi) "Microinjection into Xenopus Oocytes," Department of Biochemistry and Molecular Biology, Faculty of Medicine, The University of Tokyo, [Online], Web URL: < http://biochem2.umin.jp/contents/Manuals/manual83/manual83.html>.

* cited by examiner

*Primary Examiner*—Jyoti Nagpaul
(74) *Attorney, Agent, or Firm*—Fujitsu Patent Center

(57) ABSTRACT

A solution filling apparatus fills a capillary with solution of a substance to be introduced into a cell. A capillary holding unit holds the capillary. An injection-tube holding unit holds an injection tube to be injected into the capillary. A solution ejecting unit ejects the solution from the injection tube into the capillary. A guiding unit guides the injection tube into the capillary. A capillary oscillating unit oscillates the injection-tube holding unit and the solution ejecting unit.

7 Claims, 8 Drawing Sheets

SOLUTION FILLING APPARATUS

BACKGROUND OF THE INVENTION

1. Field of the Invention

The present invention generally relates to a technology for filling a capillary with solution of a substance to be introduced into a cell.

2. Description of the Related Art

A technique of injecting solution into a cell with a capillary is known as a microinjection technique (see, for example, Japanese Patent Application Laid-Open No. 2004-344036). In the microinjection technique, a solution, such as deoxyribonucleic acid (DNA), compounds, or chemical agents, is filled in a capillary, and the capillary is carefully penetrated into a cell and the solution is injected into the cell. The capillary is a fine needle-like glass tube with a sharp tip for penetrating in the cell. Conventionally, an operator manually fills the solution in the capillary.

The microinjection technique has been profoundly used in regenerative medical techniques or techniques of developing new drugs. As a result, it has become necessary to stock a large number of capillaries filled with solution for penetrating into cells. However, if solution is manually filled in a capillary as in the conventional technique, it is difficult to maintain the quality of filling and it is also difficult to fill a large number of capillaries in given time.

SUMMARY OF THE INVENTION

It is an object of the present invention to at least solve the problems in the conventional technology.

A solution filling apparatus according to one aspect of the present invention is for filling a capillary with solution of a substance to be introduced into a cell. The solution filling apparatus includes a capillary holding unit that holds the capillary; an injection-tube holding unit that holds an injection tube to be injected into the capillary; and a solution ejecting unit that ejects the solution from the injection tube into the capillary.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention are explained in detail below with reference to the accompanying drawings.

Figure 1:
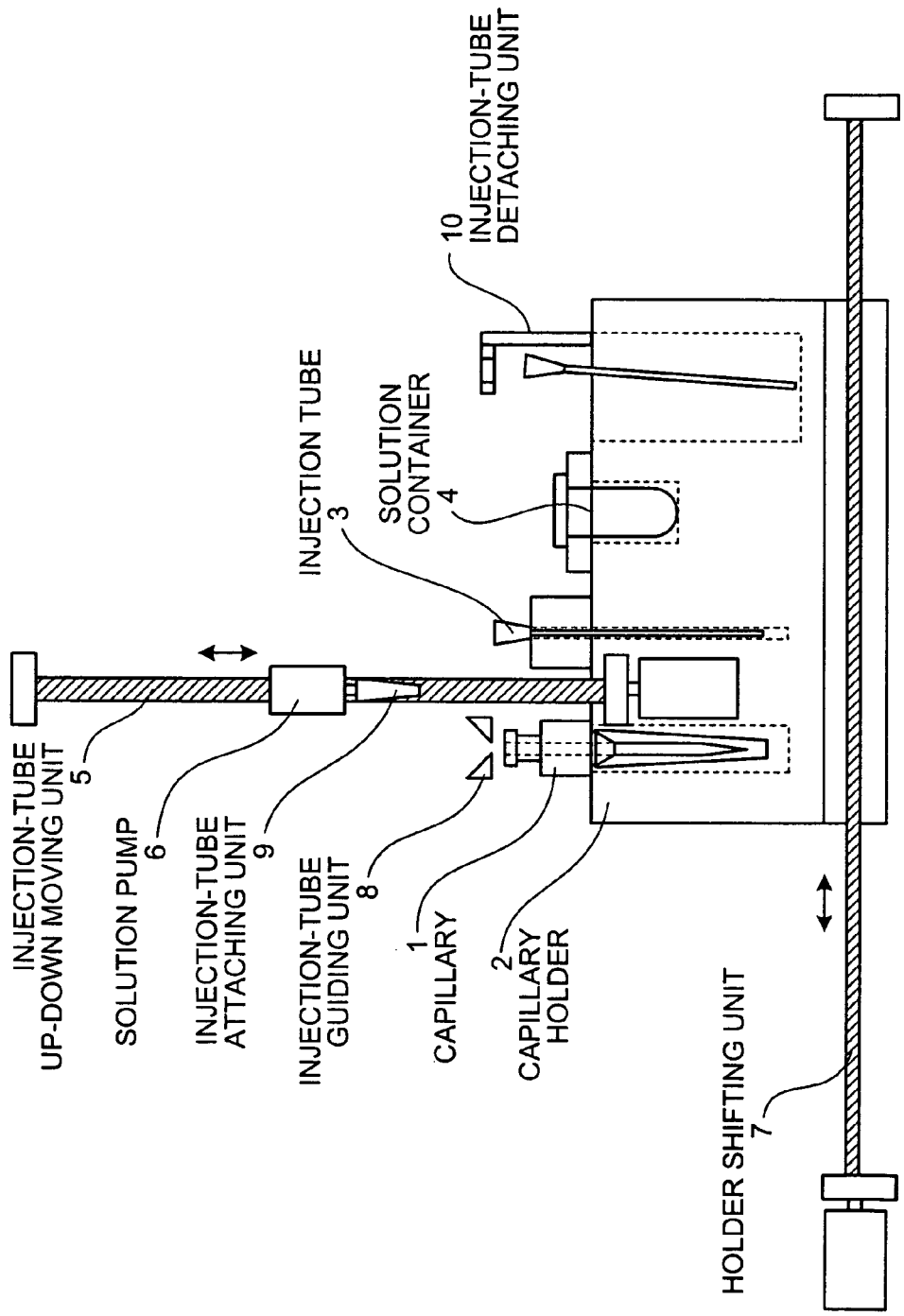
FIG. 1 is a schematic of a solution filling apparatus according to an embodiment of the present invention.

FIG. 1 is a schematic of a solution filling apparatus according to an embodiment of the present invention. A capillary holder 2 is linked to a holder shifting unit 7. An injection-tube guiding unit 8 and an injection-tube up-down moving unit 5 are arranged above the capillary holder 2. Magazines (not shown) for supporting a capillary 1, an injection tube 3, and a solution container 4, respectively, are arranged on the capillary holder 2. The solution container 4 is used for storing solution to be filled in the capillary 1. An injection-tube detaching unit 10 is arranged on the capillary holder 2. A solution pump 6 is attached to the injection-tube up-down moving unit 5. The solution pump 6 includes an injection-tube attaching unit 9.

The holder shifting unit 7 is configured to shift the capillary holder 2 in a horizontal direction, that is, in a direction orthogonal to a longitudinal axis of the capillary 1. The injection-tube up-down moving unit 5 is configured to move up or down the solution pump 6, that is, move the solution pump 6 in a direction parallel to the longitudinal axis of the capillary 1 and orthogonal to the direction of movement of the capillary holder 2.

Although the capillary 1, the injection tube 3, and the solution container 4 have been shown to be placed on one capillary holder 2, the present invention is not limited to an arrangement shown in FIG. 1. That is, the capillary 1, the injection tube 3, and the solution container 4 can be placed on separate holders. Moreover, the capillary 1, the injection tube 3, and the solution container 4 can be arranged in any order.

As long as the injection tube 3 is longer than the capillary 1, there is no particular restriction on the structure of the capillary 1, the injection tube 3, and the solution container 4. In other words, any types of capillaries, injection tubes, and solution containers can be used.

When a ball screw can be used for the holder shifting unit 7, the ball screw shifts an object in a linear manner. When a rotary table can also be used for the holder shifting unit 7, the rotary table shifts an object in a circular manner. When the rotary table is used, the capillary 1, the injection tube 3, the solution container 4, and the injection-tube detaching unit 10 need to be arranged in a circular manner. Any types of pumps can be employed for the solution pump 6, and a ball screw can be used for the injection-tube up-down moving unit 5.

The capillary 1, the injection tube 3, and the solution container 4 filled with solution to be injected into a cell are placed in respective magazines. Throughout the following process, care must be taken so that the solution remains aseptic and does not get contaminated.

Figure 2:
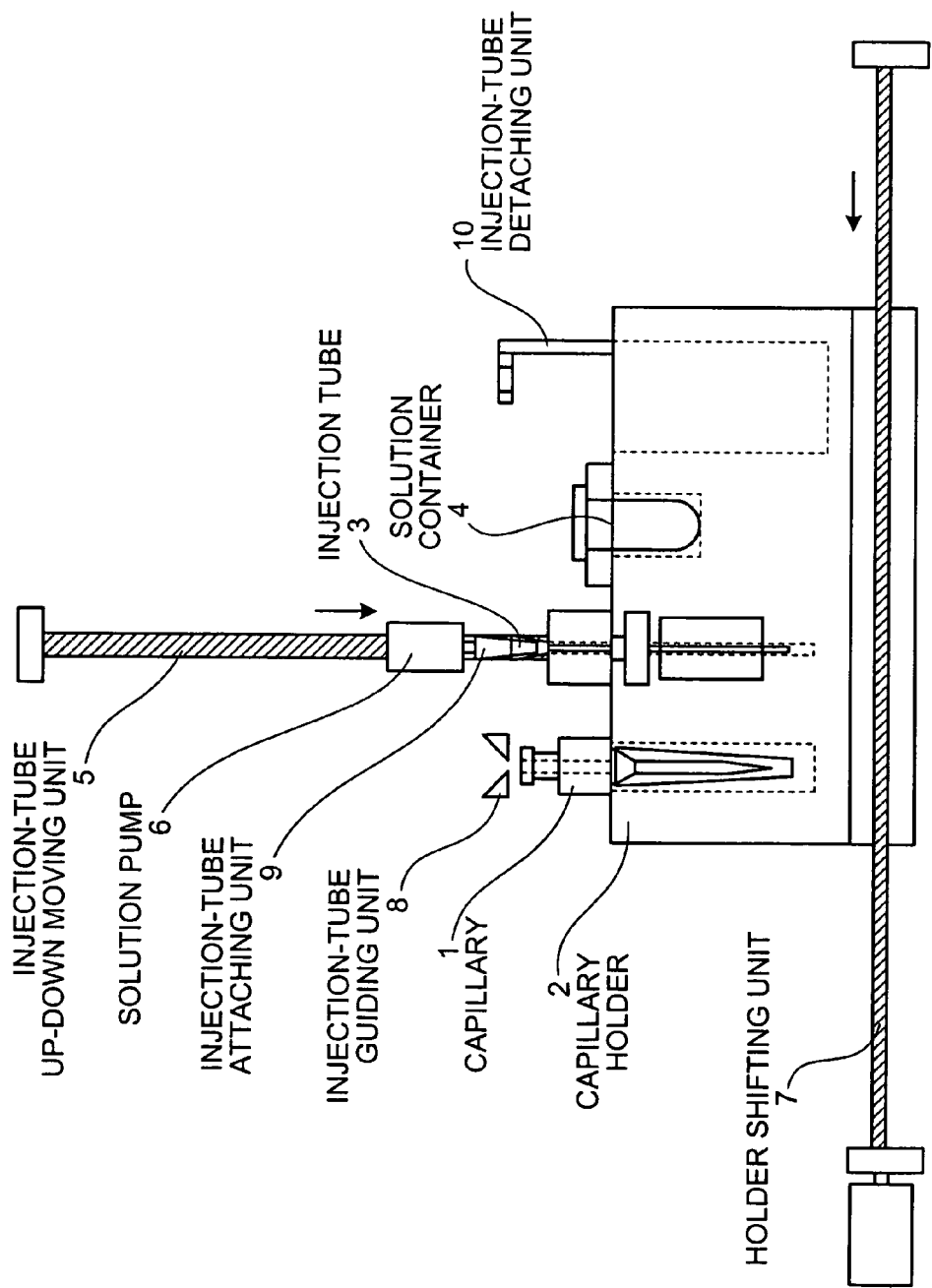
FIG. 2 is a schematic for illustrating an operation of the solution filling apparatus according to the present embodiment, matching a longitudinal axis of an injection tube with a center of an injection-tube attaching unit.

Then, as shown in FIG. 2, the holder shifting unit 7 shifts the capillary holder 2 such that the longitudinal axis of the injection tube 3 coincides with the center of the injection-tube attaching unit 9 on the solution pump 6. In this state, the injection-tube up-down moving unit 5 moves the solution pump 6 down such that the injection tube 3 gets attached to the solution pump 6.

Figure 3:
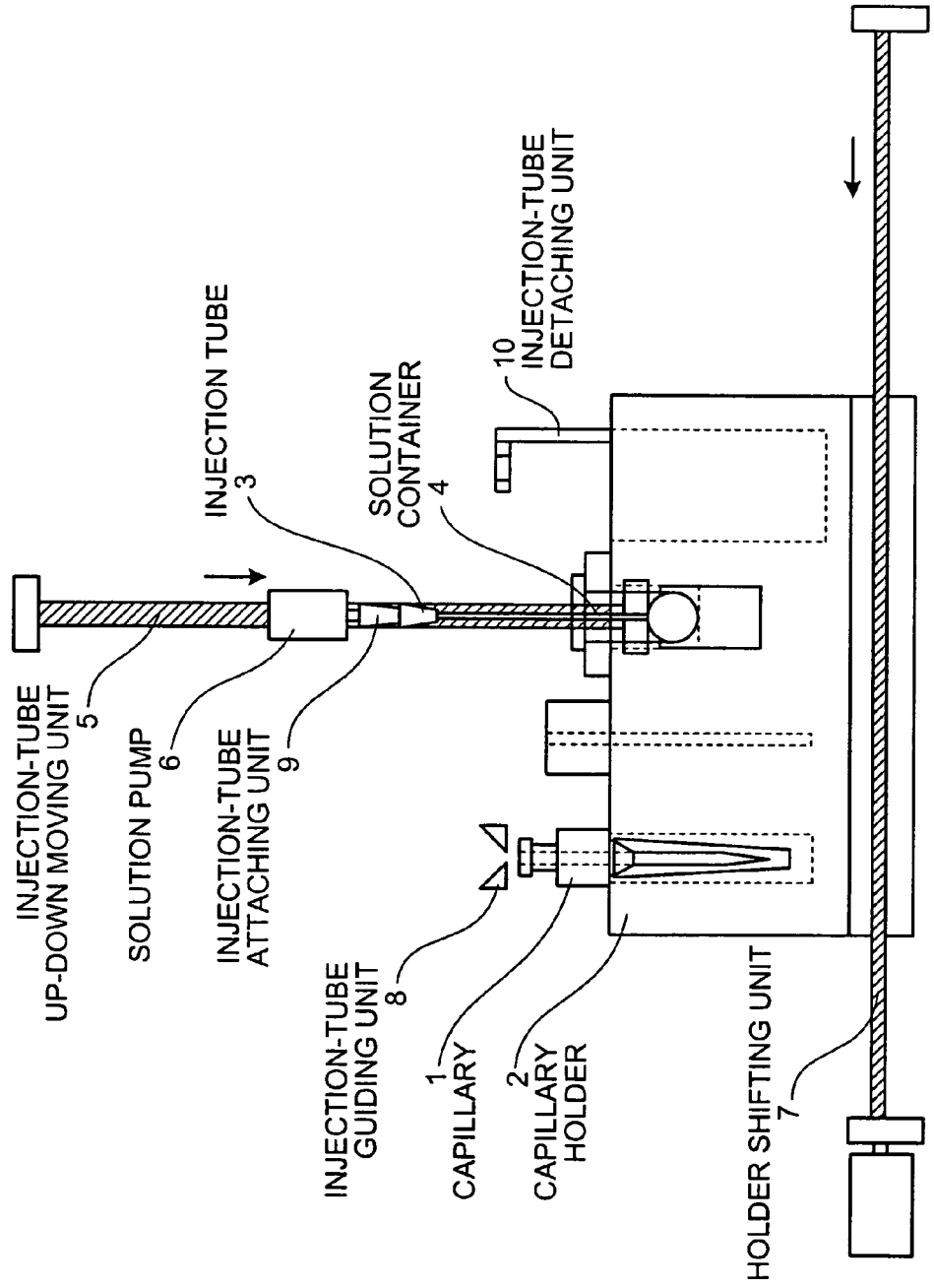
FIG. 3 is a schematic for illustrating the operation of the solution filling apparatus according to the present embodiment, matching the longitudinal axis of the injection tube with a longitudinal axis of a solution container.

Subsequently, as shown in FIG. 3, the holder shifting unit 7 shifts the capillary holder 2 such that the longitudinal axis of the solution container 4 coincides with the longitudinal axis of the injection tube 3. In this state, the injection-tube up-down moving unit 5 moves the injection tube 3 down so that a tip of the injection tube 3 is dipped in the solution in the solution container 4. Subsequently, the solution pump 6 pumps up a predetermined amount of the solution into the injection tube 3 from the solution container 4.

The injection-tube up-down moving unit 5 moves the injection tube 3 containing the solution up such that the tip of the injection tube 3 is positioned at a level above the injection-tube guiding unit 8. Then, the holder shifting unit 7 shifts the capillary holder 2 such that the longitudinal axis of the capillary 1 coincides with the longitudinal axis of the injection tube 3. The injection-tube guiding unit 8 is used for guiding the tip of the injection tube 3 in the capillary 1. There is no particular restriction on the structure of the injection-tube guiding unit 8. The injection-tube guiding unit 8 can be configured with one or more components. Moreover, the injection-tube guiding unit 8 can be a movable component, which moves along with the injection-tube up-down moving unit 5, or can be a fixed component.

Figure 4:
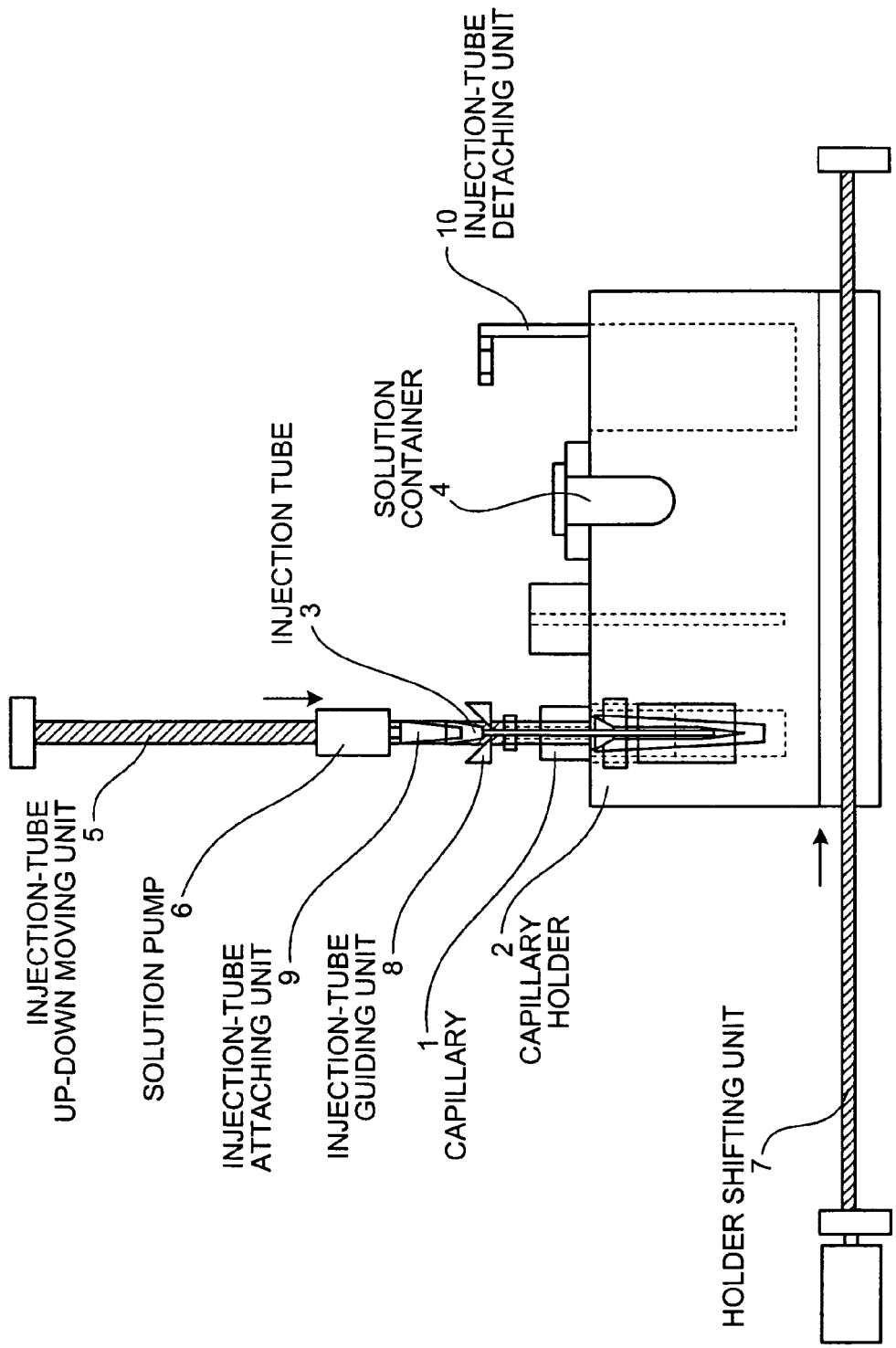
FIG. 4 is a schematic for illustrating the operation of the solution filling apparatus according to the present embodiment, injecting the injection tube into a capillary.
Figure 5:
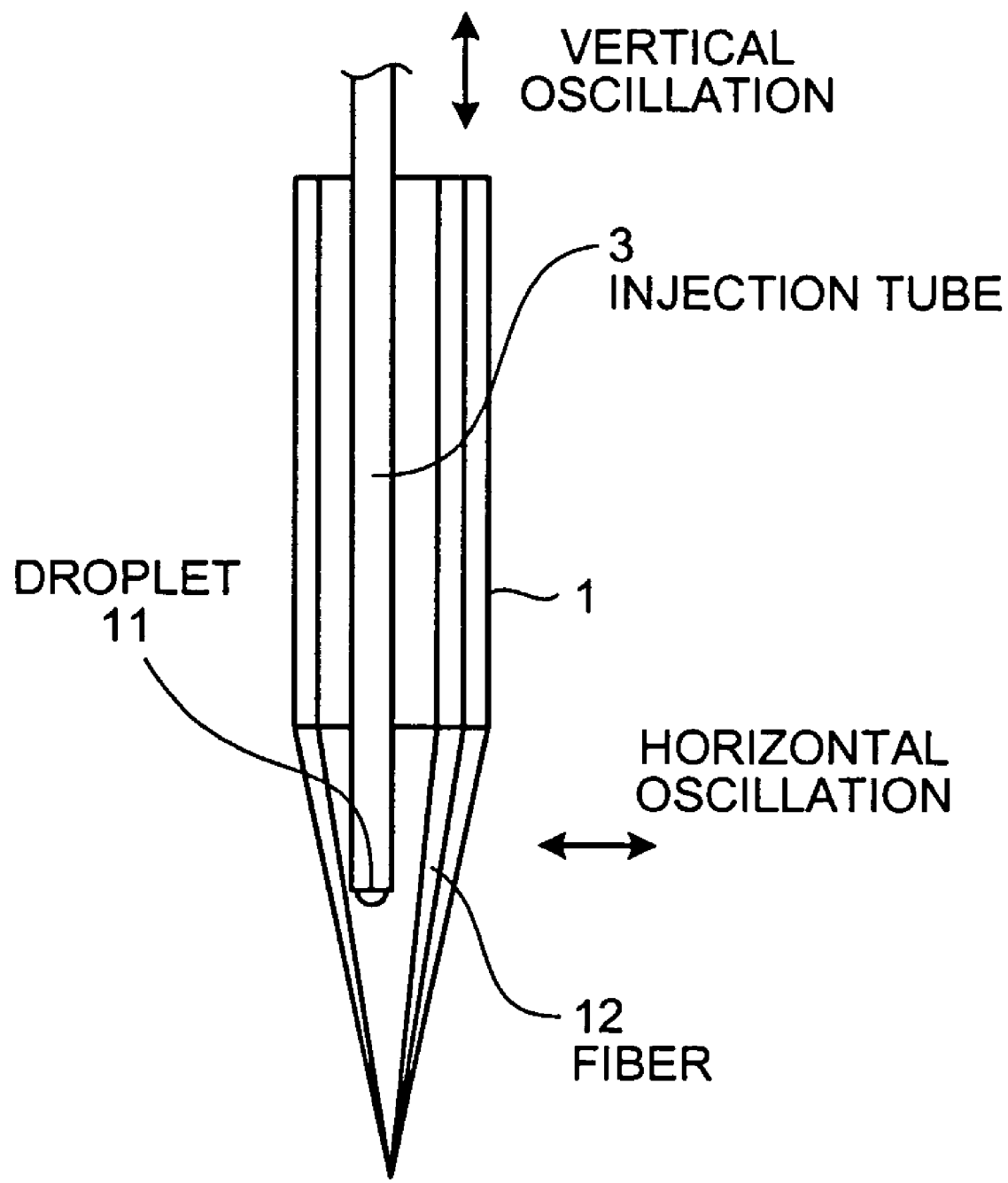
FIG. 5 is a schematic for illustrating the operation of the solution filling apparatus according to the present embodiment, oscillating the injection tube and the capillary upon injecting the solution.

Then, as shown in FIG. 4, the injection-tube up-down moving unit 5 moves the injection tube 3 down so that the tip of the injection tube 3 comes around an upper end of the capillary 1. In this state, the solution in the injection tube 3 is ejected into the capillary 1. During the ejection of the solution, the injection-tube up-down moving unit 5 and the holder shifting unit 7 conducts oscillating motions. Namely, as shown in FIG. 5, the injection tube 3 and the capillary 1 oscillate in orthogonal directions. Due to the oscillations the probability that a droplet of the solution formed at the tip of the injection tube 3 makes a contact with a fiber 12 in the capillary 1 increase. As a result, the solution can be stably filled in the capillary 1. The holder shifting unit 7 conducts the oscillatory motion, for example, with amplitude of 0.1 mm to 1 mm and with frequency of 1 Hz to 10 Hz. The injection-tube up-down moving unit 5 conducts the oscillatory motion, for example, with amplitude of 1 mm to 2 mm and with frequency of 0.5 Hz to 1 Hz.

The above state is maintained for a predetermined time, for example, 5 seconds to 10 seconds. After that, the injection-tube up-down moving unit 5 moves the injection tube 3 up to a level above the capillary 1. In this state, the holder shifting unit 7 oscillates again. As a result, if there are any air bubbles in the capillary 1, they get removed so that the capillary 1 can be completely filled with the solution.

Figure 6:
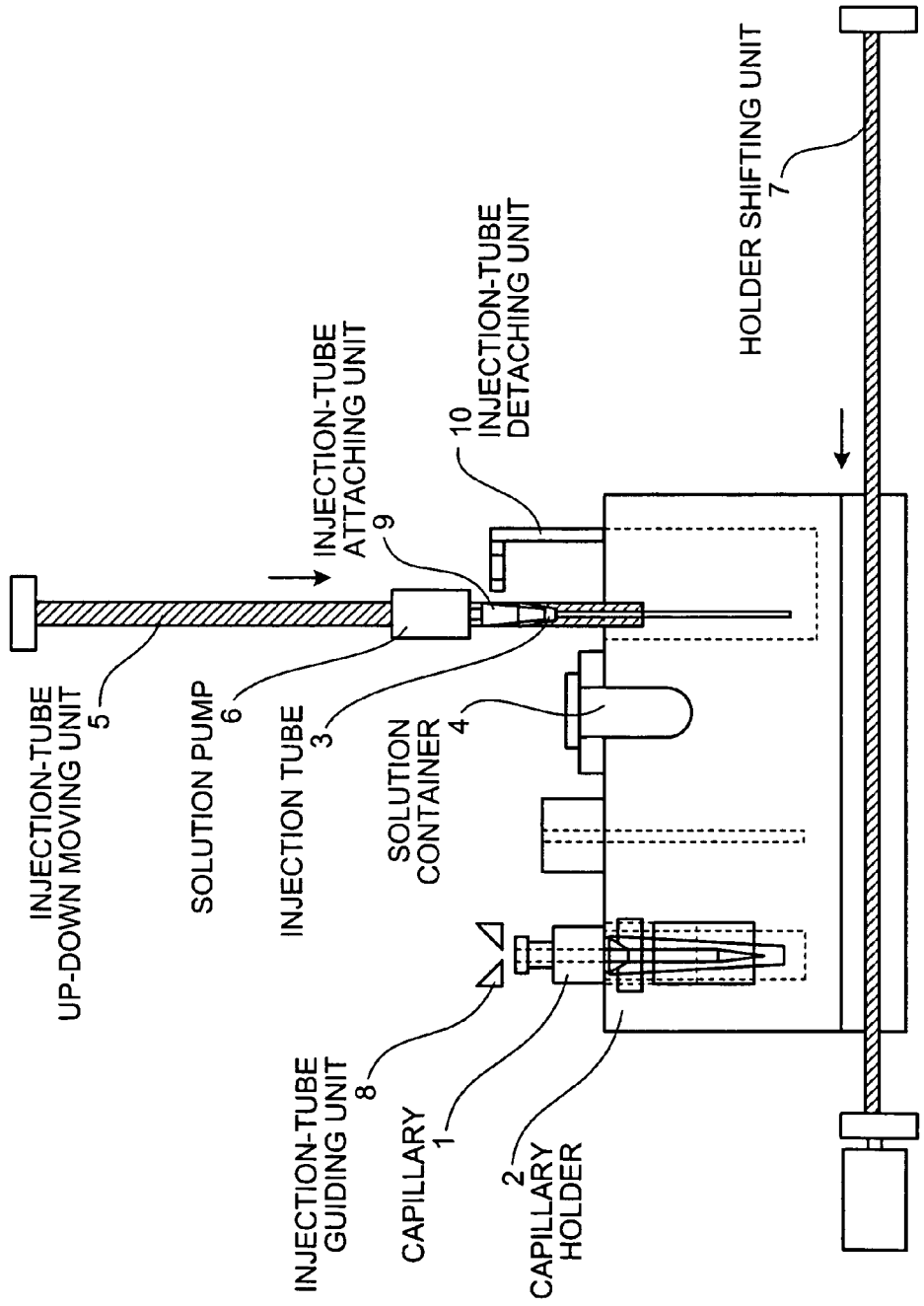
FIG. 6 is a schematic for illustrating the operation of the solution filling apparatus according to the present embodiment, matching the longitudinal axis of the injection tube with a longitudinal axis of an injection-tube detaching unit.
Figure 7:
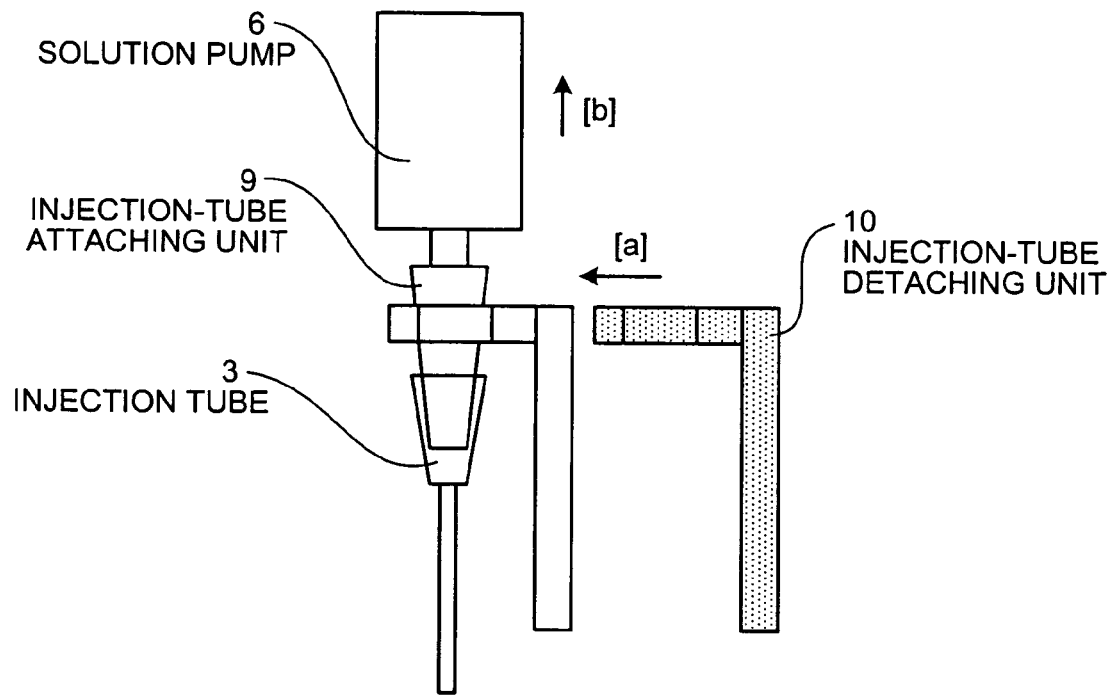
FIG. 7 is a schematic for illustrating the operation of the solution filling apparatus according to the present embodiment, detaching the injection tube from the injection-tube attaching unit.
Figure 8:
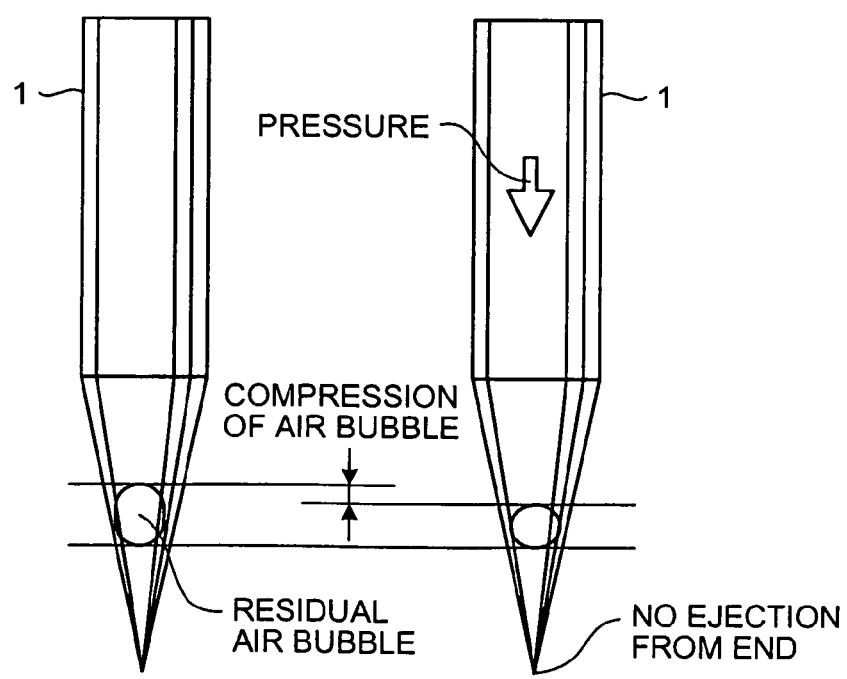
FIG. 8 is a schematic for illustrating a residual air bubble in a capillary and an effect of the air bubble.
Figure 9:
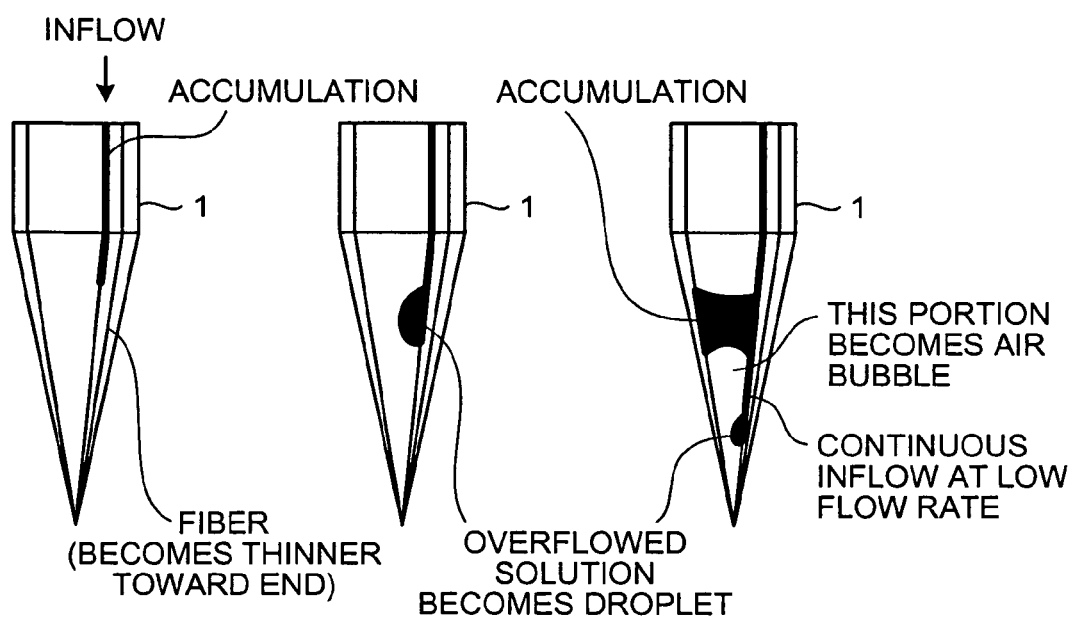
FIG. 9 is a schematic for explaining a formation of an air bubble in a process of filling the solution.

Then, the holder shifting unit 7 shifts the capillary holder 2 such that the longitudinal axis of the injection-tube detaching unit 10 coincides with the longitudinal axis of the injection tube 3. In this state, the injection-tube up-down moving unit 5 moves the injection tube 3 down so that the injection tube 3 is placed under a claw of the injection-tube detaching unit 10 as shown in FIG. 6.

Subsequently, the holder shifting unit 7 shifts the capillary holder 2 again in the horizontal direction until the injection-tube attaching unit 9 attached to the solution pump 6 reaches to the open space of the injection-tube detaching unit 10 as indicated by [a]. In this state, the injection-tube up-down moving unit 5 moves the injection tube 3 up as indicated by [b]. As the injection tube 3 moves up, the injection tube 3 is hooked on the claw of the injection-tube detaching unit 10. In this state, the injection-tube up-down moving unit 5 moves the injection tube 3 up and down. As a result the injection tube 3 is detached from the injection-tube attaching unit 9 and remains in the injection-tube detaching unit 10 as shown in FIG. 1.

The filling operation is completed with placement of the injection tube 3 in the injection-tube detaching unit 10. The same operation can be repeated for another set of capillary and injection tube.

According to an embodiment of the present invention, more capillaries can be filled in a given time as compared to the conventional manual operation, and the quality of filling can be maintained.

Furthermore, according to an embodiment of the present invention, the air bubble formed in a capillary can be effectively removed, and it is possible to prevent a case in which the solution is not properly ejected from the capillary due to the air bubble.

Although the invention has been described with respect to a specific embodiment for a complete and clear disclosure, the appended claims are not to be thus limited but are to be construed as embodying all modifications and alternative constructions that may occur to one skilled in the art that fairly fall within the basic teaching herein set forth.

What is claimed is:

1. A solution filling apparatus for filling a capillary with solution of a substance to be introduced into a cell, the solution filling apparatus comprising:
   a capillary holding unit that holds the capillary;
   an injection-tube holding unit that holds an injection tube to keep at least a tip of the injection tube inside the capillary;
   a capillary oscillating unit that oscillates the capillary holding unit in a direction perpendicular to a longitudinal axis of the capillary held by the capillary holding unit to bring an inner surface of the capillary into contact with the tip of the injection tube; and
   a solution ejecting unit that ejects the solution from the injection tube into the capillary.

2. The solution filling apparatus according to claim 1, further comprising:
   a guiding unit that guides the injection tube into the capillary.

3. The solution filling apparatus according to claim 1, wherein
   the capillary oscillating unit includes a first oscillating unit that oscillates, when the solution ejecting unit ejecting the solution from the injection tube into the capillary, the capillary holding unit in a direction perpendicular to a longitudinal axis of the capillary.

4. The solution filling apparatus according to claim 1, wherein
   the capillary oscillating unit includes a second oscillating unit that oscillates, when the solution ejecting unit ejecting the solution from the injection tube into the capillary, either one of the injection-tube holding unit and the solution ejecting unit in a direction parallel to the longitudinal axis of the capillary.

5. The solution filling apparatus according to claim 1, wherein
   the capillary oscillating unit includes a third oscillating unit that oscillates, after the solution ejecting unit ejecting the solution from the injection tube into the capillary, the capillary holding unit in the direction perpendicular to the longitudinal axis of the capillary.

6. The solution filling apparatus according to claim 1, wherein
the solution ejecting unit includes an ejecting unit that ejects the solution without decreasing an ejection rate at a time of beginning an ejection of the substance during the ejection.

7. The solution filling apparatus according to claim 1, further comprising:
a detaching unit that detaches the injection tube from the injection-tube holding unit.

* * * * *